(12) United States Patent
Ou et al.

(10) Patent No.: US 8,541,639 B2
(45) Date of Patent: *Sep. 24, 2013

(54) PROCESS FOR PRODUCING PARA-XYLENE

(75) Inventors: John Di-Yi Ou, Houston, TX (US); John R. Porter, Friendswood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/594,286

(22) Filed: Aug. 24, 2012

(65) Prior Publication Data
US 2012/0330075 A1    Dec. 27, 2012

Related U.S. Application Data

(62) Division of application No. 12/612,007, filed on Nov. 4, 2009, now Pat. No. 8,273,934.

(60) Provisional application No. 61/122,570, filed on Dec. 15, 2008.

(51) Int. Cl.
*C07C 5/27*    (2006.01)

(52) U.S. Cl.
USPC ............................... 585/478; 585/477

(58) Field of Classification Search
USPC .................................. 585/478, 477
See application file for complete search history.

(56) References Cited

U.S. PATENT DOCUMENTS

| 3,706,812 A | 12/1972 | Rosset et al. |
| 3,732,325 A | 5/1973 | Pharis et al. |
| 4,120,911 A | 10/1978 | Davidson |
| 4,886,929 A | 12/1989 | Neuzil et al. |
| 2007/0249882 A1 | 10/2007 | Ou et al. |

FOREIGN PATENT DOCUMENTS

| WO | 2007/127049 | 11/2007 |

*Primary Examiner* — Thuan D Dang
(74) *Attorney, Agent, or Firm* — Andrew B. Griffis

(57) ABSTRACT

A process for producing a PX-rich product, the process comprising: (a) providing a PX-depleted stream; (b) isomerizing at least a portion of the PX-depleted stream to produce an isomerized stream having a PX concentration greater than the PX-depleted stream and a benzene concentration of less than 1,000 ppm and a $C_9+$ hydrocarbons concentration of less than 5,000 ppm; and (c) separating the isomerized stream by selective adsorption.

4 Claims, 1 Drawing Sheet

PROCESS FOR PRODUCING PARA-XYLENE

CROSS-REFERENCE TO RELATED APPLICATIONS

This application is a divisional of U.S. application Ser. No. 13/594,286 (now U.S. Pat. No. 8,273,934), which claims the benefit of U.S. Provisional Application No. 61/122,570, filed Dec. 15, 2008, both incorporated herein by reference.

FIELD OF THE INVENTION

This invention relates to a process for producing para-xylene.

BACKGROUND OF THE INVENTION

Ethylbenzene (EB), para-xylene (PX), ortho-xylene (OX) and meta-xylene (MX) are often present together in $C_8$ aromatic product streams from chemical plants and oil refineries. Of these $C_8$ compounds, although EB is an important raw material for the production of styrene, for a variety of reasons most EB feedstocks used in styrene production are produced by alkylation of benzene with ethylene, rather than by recovery from a $C_8$ aromatics stream. Of the three xylene isomers, PX has the largest commercial market and is used primarily for manufacturing terephthalic acid and terephthalate esters for use in the production of various polymers such as poly (ethylene terephthalate), polypropylene terephthalate), and poly(butene terephthalate). While OX and MX are useful as solvents and raw materials for making products such as phthalic anhydride and isophthalic acid, market demand for OX and MX and their downstream derivatives is much smaller than that for PX.

Given the higher demand for PX as compared with its other isomers, there is significant commercial interest in maximizing PX production from any given source of $C_8$ aromatic materials. However, there are two major technical challenges in achieving this goal of maximizing PX yield. Firstly, the four $C_8$ aromatic compounds, particularly the three xylene isomers, are usually present in concentrations dictated by the thermodynamics of production of the $C_8$ aromatic stream in a particular plant or refinery. As a result, the PX production is limited, at most, to the amount originally present in the $C_8$ aromatic stream unless additional processing steps are used to increase the amount of PX and/or to improve the PX recovery efficiency. Secondly, the $C_8$ aromatics are difficult to separate due to their similar chemical structures and physical properties and identical molecular weights.

A variety of methods are known to increase the concentration of PX in a $C_8$ aromatics stream. These methods normally involve recycling the stream between a separation step, in which at least part of the PX is recovered to produce a PX-depleted stream, and a xylene isomerization step, in which the PX content of the PX-depleted stream is returned back towards equilibrium concentration, typically by contact with a molecular sieve catalyst. However, the commercial utility of these methods depends on the efficiency, cost effectiveness and rapidity of the separation step which, as discussed above, is complicated by the chemical and physical similarity of the different $C_8$ isomers.

Fractional distillation is a commonly used method for separating different components in chemical mixture. However, it is difficult to use conventional fractional distillation technologies to separate EB and the different xylene isomers because the boiling points of the four $C_8$ aromatics fall within a very narrow 8° C. range, namely from about 136° C. to about 144° C. (see Table 1 below). In particular, the boiling points of PX and EB are about 2° C. apart, whereas the boiling points of PX and MX are only about 1° C. apart. As a result, large equipment, significant energy consumption, and/or substantial recycles would be required for fractional distillation to provide effective $C_8$ aromatic separation.

TABLE I

| $C_8$ compound | Boiling Point (° C.) | Freezing Point (° C.) |
|---|---|---|
| EB | 136 | −95 |
| PX | 138 | 13 |
| MX | 139 | −48 |
| OX | 144 | −25 |

Fractional crystallization is an alternative method of separating components of a mixture and takes advantage of the differences between the freezing points and solubilities of the components at different temperatures. Due to its relatively higher freezing point, PX can be separated as a solid from a $C_8$ aromatic stream by fractional crystallization while the other components are recovered in a PX-depleted filtrate. High PX purity, a key property needed for satisfactory conversion of PX to terephthalic acid and terephthalate esters, can be obtained by this type of fractional crystallization. U.S. Pat. No. 4,120,911 provides a description of this method. Commercially available fractional crystallization processes and apparatus include the crystallization isofining process, the continuous countercurrent crystallization process, direct $CO_2$ crystallizer, and scraped drum crystallizers. Due to high utility usage and the formation of a eutectic between PX and MX, it is usually more advantageous to use a feed with as high an initial PX concentration as possible when using fractional crystallization to recover PX.

An alternative xylene separation method uses molecular sieves, such as zeolites, to selectively adsorbed para-xylene from the $C_8$ aromatic feedstream to form a PX-depleted effluent. The adsorbed PX can then be desorbed by various ways such as heating, lowering the PX partial pressure or stripping. (See generally U.S. Pat. Nos. 3,706,812, 3,732,325 and 4,886,929). Two commercially available processes used in many chemical plants or refineries are PAREX™ and ELUXYL™ processes. Both processes use molecular sieves to adsorb PX. In such molecular-sieve based adsorption processes, a higher amount of PX, typically over 90%, compared with that from a fractional crystallization process, typically below 65%, may be recovered from the PX present in a particular feed.

For many of these PX separation processes, the higher the original PX concentration in the feed stream, the easier, more efficient and more economical it becomes to perform the PX separation. Therefore, there are strong economic and technical incentives to increase the PX concentration in a hydrocarbon feed stream comprising the $C_8$ aromatic compounds prior to sending the feed stream to a PX recovery unit.

Known technologies integrate selective adsorption and fractional crystallization in PX separation and isomerization loops. For example, U.S. Publication No. 2007/0249882 teaches a process whereby a $C_8$-rich stream is fed to both selective adsorption and fractional crystallization recovery units. By taking advantage of the higher recovery rates of the selective adsorption unit, the PX-depleted effluent (which is typically below 65% depleted) from the fractional crystallization recovery unit can be fed to the selective adsorption unit. While this yields greater efficiency, further advancements were achieved by increasing the $C_8$ concentration of the fractional crystallization PX-depleted effluent stream prior to further recovery by selective adsorption. This was achieved by a xylene isomerization step between the fractional crystallization and the selective adsorption units. Furthermore, liquid-phase isomerization was preferred in this step because of cost, simplicity (no need for hydrogen recycle), and low xylene loss.

The liquid-phase isomerization of $C_8$ aromatics to increase the PX concentration is temperature dependent. That is, the conversion efficiency to PX increases with increasing temperature with the primary controlling limitation being the ability to maintain a liquid state. Although increased system pressure can allow for higher temperatures, physical and cost constraints ultimately place limitations on the process. As a result, liquid-phase isomerization typically operates near 300° C. and at pressures above 300 psig.

While integrated systems of this type yield advantageous efficiencies, the selective adsorption unit is intolerant to $C_7$- hydrocarbons, particularly benzene, and $C_9$+ aromatic compounds (9 or more carbons aromatic compounds). In fact, most selective adsorption units commercially employed can only tolerate up to about 300 ppm of benzene and less than 5000 ppm $C_9$+ aromatic compounds. Thus, the production of $C_7$- hydrocarbons or $C_9$+ aromatics by liquid-phase isomerization processes, particularly those positioned between fractional crystallization and selective adsorption, presents additional problems for overall process efficiency.

SUMMARY OF THE INVENTION

Embodiments of the present invention provide a process for producing a PX-rich product, the process comprising: (a) separating a feedstock containing $C_8$ hydrocarbons to produce a $C_8$ hydrocarbons rich stream; (b) separating a first portion of the $C_8$ hydrocarbons rich stream to produce a first PX-rich stream and a first raffinate stream; (c) isomerizing at least a portion of the first raffinate stream to produce a first isomerized stream having a higher PX concentration than the first raffinate stream; (d) separating a second portion of the $C_8$ hydrocarbons rich stream to produce a second PX-rich stream and a second raffinate stream; (e) isomerizing, at least partially in the liquid phase, at least a portion of the second raffinate stream to produce a second isomerized stream having a higher PX concentration than the second raffinate stream, where the second isomerized stream has a benzene concentration of less than 1,000 ppm and a $C_9$+ hydrocarbons concentration of less than 5,000 ppm; (f) recovering at least a portion of at least one of the first and second PX-rich streams as PX-rich product; and (g) providing at least a portion of the first isomerized stream and at least a portion of the second isomerized stream to the separating (a).

Other embodiments provide a process for producing a PX-rich product, the process comprising: (a) separating a feedstock containing $C_8$ hydrocarbons to produce a $C_8$ hydrocarbons rich stream; (b) separating a first portion of the $C_8$ hydrocarbons rich stream to produce a first PX-rich stream and a first raffinate stream; (c) isomerizing at least a portion of the first raffinate stream to produce a first isomerized stream having a higher PX concentration than the first raffinate stream; (d) separating the first isomerized stream to produce a second $C_8$ hydrocarbons rich stream; (e) separating the second $C_8$ hydrocarbons rich stream to produce a second PX-rich stream and a second raffinate stream; (f) isomerizing, at least partially in the liquid phase, at least a portion of the second raffinate stream to produce a second isomerized stream having a higher PX concentration than the second raffinate stream; and (g) providing at least a portion of the second isomerized stream to the separating (a).

Other embodiments provide a process for producing a PX-rich product, the process comprising: (a) separating a feedstock containing $C_8$ hydrocarbons to produce a $C_8$ hydrocarbons rich stream; (b) separating a first portion of the $C_8$ hydrocarbons rich stream to produce a first PX-rich stream and a first raffinate stream; (c) isomerizing at least a portion of the first raffinate stream to produce a first isomerized stream having a higher PX concentration than the first raffinate stream; (d) separating the first raffinate stream to produce a second $C_8$ hydrocarbons rich stream; (e) separating the second $C_8$ hydrocarbons rich stream to produce a second PX-rich stream and a third stream; (f) isomerizing, at least partially in the liquid phase, at least a portion of the second raffinate stream to produce a second isomerized stream having a higher PX concentration than the second raffinate stream, where the second isomerized stream has a benzene concentration of less than 1,000 ppm and a $C_9$+ hydrocarbons concentration of less than 5,000 ppm; and (g) providing at least a portion of the second isomerized stream to the separating (a).

Other embodiments provide a PX-production process where a $C_8$ hydrocarbon rich stream is separated into a PX-rich stream and a PX-depleted stream by fractional crystallization, and where the PX-depleted stream is subsequently isomerized to increase the concentration of PX in the PX-depleted stream for subsequent separation by selective adsorption, the improvement comprising isomerizing said PX-depleted stream in the liquid phase to produce a stream having a higher PX concentration than the PX-depleted stream, a benzene concentration of less than 500 ppm, and a $C_9$+ concentration of less than 5,000 ppm.

Other embodiments provide a process for producing a PX-rich product, the process comprising: (a) providing a PX-depleted stream; (b) isomerizing at least a portion of the PX-depleted stream to produce an isomerized stream having a PX concentration greater than the PX-depleted stream and a benzene concentration of less than 1,000 ppm and a $C_9$+ hydrocarbons concentration of less than 5,000 ppm; and (c) separating the isomerized stream by selective adsorption.

DETAILED DESCRIPTION OF THE INVENTION

Figure 1:
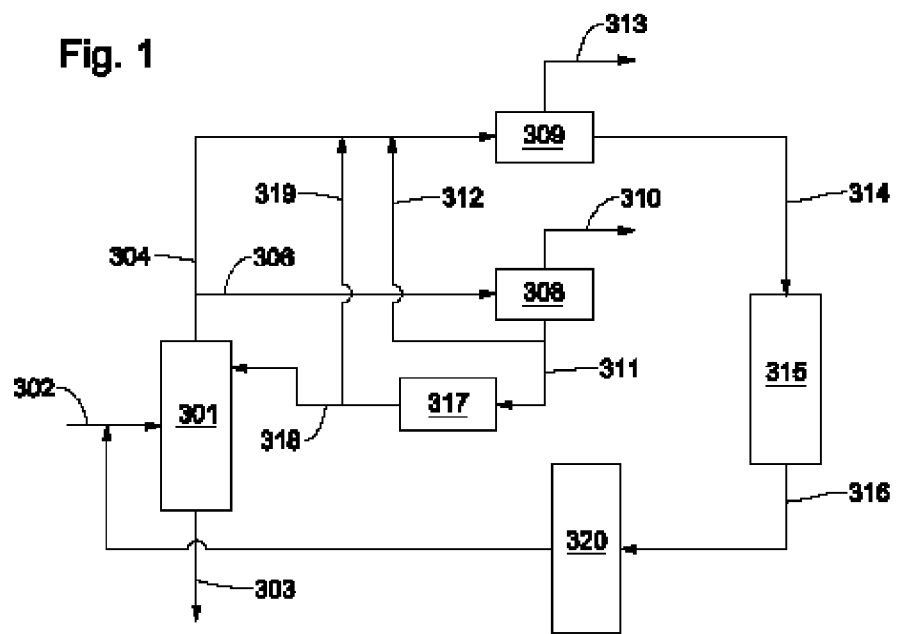
FIG. 1 is a schematic diagram of a producing para-xylene by employing integrated fractional crystallization and selective adsorption according to one or more embodiments of the present invention.

All patents, patent applications, test procedures, priority documents, articles, publications, manuals, and other documents cited herein are fully incorporated by reference to the extent such disclosure is not inconsistent with the present application and for all jurisdictions in which such incorporation is permitted.

When numerical lower limits and numerical upper limits are listed herein, ranges from any lower limit to any upper limit are contemplated.

One having ordinary skill in the art understands that the embodiments discussed in this application do not represent all the possible apparatus or process variations embodied by the present disclosure. In addition, many pieces of equipment and apparatus and certain processing steps may be needed for industrial, commercial or even experimental purposes. Examples of such equipments and apparatus and processing steps are, but not limited to, distillation columns, fractionation columns, heat exchanges, pumps, valves, pressure gauges, temperature gauges, liquid-vapor separators, feed and product driers and/or treaters, clay treaters, feed and/or product storage facilities, and processes and steps for process control. While such equipment, apparatus and steps that are not needed for understanding the essence of the present application are not shown in the drawings, some of them may be mentioned from time to time to illustrate various aspects of the disclosure. It is also noted that some of the equipment may be placed at different places in the process depending on the conditions of the processes.

As used herein, the term "$C_8+$ hydrocarbons" means hydrocarbons having eight or more carbon atoms per molecule. A $C_8+$ hydrocarbons feed and/or product is a hydrocarbon feed and/or product having more than 10 wt. %, such as more than 20 wt. %, for example more than 40 wt. %, such as more than 50 wt. %, and in some cases more than 80 wt. %, $C_8+$ hydrocarbons in the feed and/or product. The term "$C_9+$ hydrocarbons" as used herein means hydrocarbons having nine or more carbon atoms per molecule and includes $C_9+$ aromatics, which are aromatic compounds including 9 or more carbon atoms per molecule. A $C_9+$ hydrocarbons feed and/or product is a hydrocarbon feed and/or product having more than 10 wt. %, such as more than 20 wt. %, for example more than 40 wt. %, such as more than 50 wt. %, and in some cases more than 80 wt. %, $C_9+$ hydrocarbons in the feed and/or product. The term "$C_7-$ hydrocarbons" as used herein means hydrocarbons having seven or less carbon atoms per molecule. A $C_7-$ hydrocarbons feed and/or product is a hydrocarbon feed and/or product having more than 10 wt. %, such as more than 20 wt. %, for example more than 40 wt. %, such as more than 50 wt. %, and in some cases more than 80 wt. %, $C_7-$ hydrocarbons in the feed and/or product. The term "$C_8$ hydrocarbons" as used herein means hydrocarbons having eight carbon atoms per molecule, including PX. A $C_8$ hydrocarbons feed and/or product, with the exception of a PX-rich or PX-depleted stream and/or product, is a hydrocarbon feed and/or product having more than 10 wt. %, such as more than 20 wt. %, for example more than 40 wt. %, such as more than 50 wt. %, and in some cases more than 80 wt. %, $C_8$ hydrocarbons in the feed and/or product. The term "$C_8$ aromatic hydrocarbons" as used herein means aromatic hydrocarbons having eight carbon atoms per molecule, i.e., xylene(s) and/or EB. A $C_8$ aromatic hydrocarbons feed and/or product, with the exception of a PX-rich or PX-depleted stream and/or product, is a hydrocarbon feed and/or product having more than 10 wt. %, such as more than 20 wt. %, for example more than 40 wt. %, such as more than 50 wt. %, and in some cases more than 80 wt. %, $C_8$ aromatic hydrocarbons in the feed and/or product.

The term "PX-depleted" means that PX concentration in an exiting stream of a particular unit is lowered as compared to the concentration in a feed stream to the same unit. It does not mean that all of PX has to be depleted or removed from the xylenes-containing feed stream(s) to the unit. The term "PX-rich" means that PX concentration in an exiting stream of a particular unit is increased as compared to the concentration in a feed stream to the same unit. It does not mean that the PX concentration has to be 100%.

Feedstock

The feedstock employed in the present process may be any $C_8+$ hydrocarbon feedstock containing $C_8$ aromatic hydrocarbons, such as a reformate stream, a hydrocracking product stream, a xylene or EB reaction product stream, an aromatic alkylation product stream, an aromatic disproportionation stream, an aromatic transalkylation stream, and/or a Cyclar™ process stream. The feedstock may further comprise recycle stream(s) from the isomerization step(s) and/or various separating steps. The $C_8+$ hydrocarbon feedstock comprises PX, together with MX, OX, and/or EB. In addition to xylenes and EB, the $C_8+$ hydrocarbon feedstock may also contain certain amounts of other aromatic or even non-aromatic compounds. Examples of such aromatic compounds are benzene, toluene and $C_9+$ aromatics such as mesitylene, pseudo-cumene and others. These types of feedstream(s) are described in "Handbook of Petroleum Refining Processes", Eds. Robert A. Meyers, McGraw-Hill Book Company, Second Edition, all relevant parts of which are hereby incorporated by reference.

Process Description

In one or more embodiments, the process of the present application comprises an initial separating step that serves to remove the $C_9+$ hydrocarbons from the $C_8+$ hydrocarbon feedstock. Because of the differences in molecular weights, boiling points and other physical and chemical properties, the $C_9+$ hydrocarbons compounds, aromatic or non-aromatic, can be separated relatively easily from the xylenes and EB. Generally, therefore, the first separating step includes fractional distillation, although other separation methods, such as crystallization, adsorption, a reactive separation, a membrane separation, extraction, or any combination thereof, can also be used. These separation methods are described in "Perry's Chemical Engineers' Handbook", Eds. R. H. Perry, D. W. Green and J. O. Maloney, McGraw-Hill Book Company, Sixth Edition, 1984, and "Handbook of Petroleum Refining Processes", Eds. Robert A. Meyers, McGraw-Hill Book Company, Second Edition, all relevant parts of which are hereby incorporated by reference.

In one or more embodiments, after removal of the $C_9+$ hydrocarbons, the process comprises at least one separating step to recover a PX-rich product stream from the resultant $C_8$ hydrocarbon stream. In one embodiment, the PX-rich product stream comprises at least 50 wt. % PX, preferably at least 60 wt. % PX, more preferably at least 70 wt. % PX, even preferably at least 80 wt. % PX, still even preferably at least 90 wt. % PX, and most preferably at least 95 wt. % PX, based on the total weight of the PX-rich product stream.

In one or more embodiments, the separating step to recover the PX-rich product stream is performed in a PX recovery unit comprising at least one a crystallization unit, an adsorption unit such as a PAREX™ unit or an ELUXYL™ unit, a reactive separation unit, a membrane separation unit, an extraction unit, a distillation unit, a fractionation unit, or any combination thereof. These types of separation unit(s) and their designs are described in "Perry's Chemical Engineers' Handbook", Eds. R. H. Perry, D. W. Green and J. O. Maloney, McGraw-Hill Book Company, Sixth Edition, 1984, and "Handbook of Petroleum Refining Processes", Eds. Robert A. Meyers, McGraw-Hill Book Company, Second Edition, all relevant parts of which are hereby incorporated by reference.

In one or more embodiments, further separating steps employed in the present process serve to separate a $C_8$ hydrocarbon feedstream into a PX-rich effluent stream and a PX-depleted stream. These separating steps may be performed in separating units comprising at least one of a crystallization unit, an adsorption unit such as a PAREX™ unit or an ELUXYL™ unit, a reactive separation unit, a membrane separation unit, an extraction unit, a distillation unit, a fractionation unit, or any combination thereof. These types of separation unit(s) and their designs are described in "Perry's Chemical Engineers' Handbook", Eds. R. H. Perry, D. W. Green and J. O. Maloney, McGraw-Hill Book Company, Sixth Edition, 1984, and "Handbook of Petroleum Refining Processes", Eds. Robert A. Meyers, McGraw-Hill Book Company, Second Edition, all relevant parts of which are hereby incorporated by reference.

In one or more embodiments, the process of the present application includes at least two isomerization steps, in each of which a feed stream comprising $C_8$ aromatic compounds is isomerized to produce an isomerization effluent. Typically, the feed stream to each isomerization step comprises PX in a concentration below its equilibrium concentration relative to other inter-convertible $C_8$ aromatic compounds under the isomerization conditions. Each catalyzed isomerization step serves to increase the PX concentration to near its equilibrium level. The isomerization step may also serve to convert part or all of EB present in the feed stream to benzene and light hydrocarbons (i.e., hydrocarbons having less than 6 carbons per molecule). Alternatively, the isomerization step may also serve to isomerize part or all of EB present in the feed stream to xylene(s).

There are many catalysts or combinations of catalysts that can be used in each isomerization step to effect the desired reaction. There are generally two types of xylene isomerization catalysts. One type of isomerization catalyst can more or less equilibrate the four different $C_8$ aromatic compounds, including EB, to the concentrations dictated by thermodynamics under the reaction conditions. This allows maximum formation of PX from $C_8$ aromatics in a particular feed. Examples of these type catalysts include IFP/Engelhard Octafining™ and Octafining II™ catalysts used in the respective processes. The other type of xylene isomerization catalyst can effect EB conversion in addition to xylene isomerization, generally in the presence of hydrogen. As discussed earlier, this type of catalyst will remove EB and produce benzene and ethane as byproducts. This may be a desirable disposition of EB, depending on supplies and demands of various products as well as other equipment present in a particular plant. Examples include Mobil High Temperature Isomerization (MHTI™) catalysts, Mobil High Activity Isomerization catalysts (MHAI™) and UOP ISOMAR™ I-100 catalysts.

A number of suitable isomerization reactors may be used for the present disclosure. Some non-limiting examples are described in U.S. Pat. Nos. 4,899,011 and 4,236,996.

For the present disclosure, a xylene isomerization reaction may be carried out in a liquid phase, a vapor (gas) phase, a super critical phase, or a combination thereof. The selection of isomerization reaction conditions and the specific composition of the aromatic feed stream being isomerized determine the physical state of the aromatic feed stream in the xylene isomerization reactor.

In one or more embodiments, the present invention provides a PX-production and recovery system that includes an integrated selective adsorption and fractional crystallization loop with a liquid-phase isomerization process that treats the PX-depleted effluent from the fractional crystallization process. In one or more embodiments, the liquid-phase isomerization process is manipulated to reduce the production of $C_7-$ hydrocarbon byproducts, particularly benzene, and $C_9+$ aromatic byproducts from the liquid-phase isomerization process. Practice of the present invention yields an overall system that is unexpectedly more efficient than prior art systems.

An exemplary process according to one embodiment of the present invention can be described with reference to FIG. 1, which includes a first separating unit 301, which may be one or more distillation columns. Separating unit receives a $C_8+$ aromatic hydrocarbon feed stream from line 302 and separates the feed into an overhead vapor stream via line 304 and a bottom liquid stream via line 303. The bottom liquid stream is composed mainly of $C_9+$ hydrocarbons (e.g., $C_9+$ aromatics) and some ortho-xylene (OX), and it is removed from the first separating unit 301 through line 303 for further processing such as distillations for OX recovery. The overhead stream is composed mainly of $C_8$ aromatic hydrocarbons (typically about 50% meta xylene (MX), about 20% PX, about 15% OX and about 15% EB) and is removed from the first separating unit 301 through line 304 and is sent for PX recovery.

PX recovery in the process shown in FIG. 1 is effected by both a fractional crystallization unit 308 and a selective adsorption unit 309. Thus at least one part of the $C_8$ aromatic hydrocarbon removed from the first separating unit 301 through line 304 is fed by line 306 to the fractional crystallization unit 308, where a first PX-rich product stream is recovered through line 310 and a PX-depleted raffinate stream is withdrawn via line 311.

The remainder of the $C_8$ aromatic hydrocarbon removed from the first separating unit 301 is fed to the selective adsorption unit 309 through line 304. In one or more embodiments, the $C_8$ aromatic hydrocarbon removed from first separating unit 301 is combined with the PX-depleted raffinate stream from fractional crystallization unit 308, which may be combined at line 304 via line 312. From selective adsorption unit 309, a second PX-rich stream is recovered through line 313 and a further PX-depleted (raffinate) stream is withdrawn via line 314. The further PX-depleted stream is fed by line 314 to a xylene isomerization unit 315 where the stream is converted into an isomerized stream having higher PX concentration than that of the further stream.

The isomerized stream is removed from the xylene isomerization unit 315 by line 316 and is fed to separation unit 301 optionally through line 302. In one or more embodiments, one or more separating units 320 may optionally be provided between the xylene isomerization unit 315 and first separating unit 301 to remove constituents such as $C_7-$ hydrocarbons or $C_9+$ hydrocarbons that may be generated by the xylene isomerization unit 315.

A second xylene isomerization unit 317 treats all or part of the PX-depleted raffinate stream withdrawn from the fractional crystallization unit 308 via line 311. When unit 317 treats part of the PX-depleted raffinate stream, the remaining portion of the raffinate stream could be sent to the selective adsorption unit 309 via line 312 and optionally 304.

In one or more embodiments, second xylene isomerization unit 317 is a liquid-phase isomerization unit. The effluent stream from the second xylene isomerization unit 317, which has a higher PX concentration than the PX-depleted raffinate stream, is withdrawn through line 318 and ultimately fed to selective adsorption unit 309. In this way, the overall PX content of the feed to selective adsorption unit 309 can be increased. In one or more embodiments, the liquid-phase isomerization product contains mostly equilibrium or near equilibrium xylene.

In one or more embodiments, all or part of the effluent stream from second xylene isomerization unit 317 is sent directly to first separating unit 301 via 318. In one or more embodiments, line 318 may direct the effluent to a tray position to affect the separation of $C_8$ and $C_9+$ hydrocarbons.

In other embodiments, all or part of the effluent stream from second xylene isomerization unit 317 is sent directly to selective adsorption unit 309 via line 319 and optionally line 304. In one or more embodiments, the effluent stream from second xylene isomerization unit 317 (i.e., the isomerized stream) is sent directly to selective adsorption unit 309 without further processing (particularly processing to remove or reduce $C_7-$ or $C_9+$ hydrocarbons). In other embodiments, the isomerized stream from isomerization unit 317 is further treated, such as by fractionation, to remove at least a part of the $C_7-$ and $C_9+$ hydrocarbons formed in isomerization unit 317 and then sent directly to selective adsorption unit 309.

In one or more embodiments, the operation of liquid-phase isomerization unit 317 is manipulated to produce a PX-rich stream having less than 1,000 ppm, in other embodiments less than 500 ppm, and in other embodiments less than 300 ppm, and in other embodiments less than 250 ppm benzene.

In one or more embodiments, the operation of liquid-phase isomerization unit 317 is manipulated to produce a PX-rich stream having less than 5,000 ppm in other embodiments less than 4,000 ppm, in other embodiments less than 3,000 ppm, in other embodiments less than 2,000 ppm, in other embodiments less than 1,000 ppm, and in other embodiments less than 500 ppm $C_9+$ hydrocarbons (e.g., $C_9+$ aromatics).

In one or more embodiments, liquid-phase isomerization unit 317 is operated at or below 300° C., in other embodiments below 280° C., and in other embodiments below 260° C. In these or other embodiments, liquid-phase isomerization unit 317 is operated at or above 150° C., in other embodiments above 175° C., and in other embodiments above 200° C.

In one or more embodiments, liquid-phase isomerization unit 317 is operated at a pressure below 350 psi, in other embodiments below 300 psi, and in other embodiments below 270 psi. In these or other embodiments, liquid-phase isomerization unit 317 is operated at a pressure above 30 psi, in other embodiments above 75 psi, and in other embodiments above 125 psi.

In one or more embodiments, the flow rate of the PX-depleted raffinate stream through isomerization unit 317 is at least 0.1 weight hourly space velocity (WHSV), in other embodiments at least 1.0 WHSV, in other embodiments at least 2.0 WHSV, and in other embodiments at least 5.0 WHSV. In these or other embodiments, the flow rate of the PX-depleted raffinate stream through isomerization unit 317 is less than 100 WHSV, and in other embodiments less than 50 WHSV, in other embodiments less than 10 WHSV.

In one or more embodiments, liquid-phase isomerization unit 317 includes a solid acid catalyst. Solid acid is described by the Brønsted and Lewis definitions as any material capable of donating a proton or accepting an electron pair. This description can be found in K. Tanabe. *Solid Acids and Bases: their catalytic properties*. Tokyo: Kodansha Scientific, 1970, p. 1-2. This reference is incorporated herein by reference in its entirety. The solid acid suitable for this invention can comprise at least one of solid acid, supported acid, or mixtures thereof. The solid acid can comprise nonporous, microporous, mesoporous, macroporous or as a mixture thereof. These porosity designations are IUPAC conventions and are defined in K. S. W. Sing, D. H. Everett, R. A. W. Haul L. Moscou, R. A. Pierotti, J. Rouquérol, T. Siemieniewska, *Pure&Appl. Chem.* 1995, 57(4), pp. 603-619, which is incorporated herein by reference in its entirety.

Non-limiting examples of solid acid components are natural clays such as kaolinite, bentonite, attapulgite, montmorillonite, clarit, fuller's earth, cation exchange resins and $SiO_2.Al_2O_3$, $B_2O_3.Al_2O_3$, $Cr_2O_3.Al_2O_3$, $MoO_3.Al_2O_3$, $ZrO_2.SiO_2$, $Ga_2O_3.SiO_2$, $BeO.SiO_2$, $MgO.SiO_2$, $CaO.SiO_2$, $SrO.SiO_2$, $Y_2O_3.SiO_2$, $La_2O_3.SiO_2$, $SnO.SiO_2$, $PbO.SiO_2$, $MoO_3.Fe_2(MoO_4)_3$, $MgO.B_2O_3$, $TiO_2.ZnO$, $ZnO$, $Al_2O_3$, $TiO_2$, $CeO_2$, $As_2O_3$, $V_2O_5$, $SiO_2$, $Cr_2O_3$, $MoO_3$, $ZnS$, $CaS$, $CaSO_4$, $MnSO_4$, $NiSO_4$, $CuSO_4$, $CoSO_4$, $CdSO_4$, $SrSO_4$, $ZnSO_4$, $MgSO_4$, $FeSO_4$, $BaSO_4$, $KHSO_4$, $K_2SO_4$, $(NH_4)_2SO_4$, $Al_2(SO_4)_3$, $Fe_2(SO_4)_3$, $Cr_2(SO_4)_3$, $Ca(NO_3)_2$, $Bi(NO_3)$, $Zn(NO_3)_2$, $Fe(NO_3)_3$, $CaCO_3$, $BPO_4$, $FePO_4$, $CrPO_4$, $Ti_3(PO_4)_4$, $Zr_3(PO_4)_4$, $Cu_3(PO_4)_2$, $Ni_3(PO_4)_2$, $AlPO_4$, $Zn_3(PO_4)_2$, $Mg_3(PO_4)_2$, $AlCl_3$, $TiCl_3$, $CaCl_2$, $AgCl_2$, $CuCl$, $SnCl_2$, $CaF_2$, $BaF_2$, $AgClO_4$, and $Mg(ClO_4)_2$. Depending on the synthesis conditions, these materials can be prepared as nonporous, microporous, mesoporous, or macroporous, as defined in the reference cited above. Conditions necessary to these preparations are known to those of ordinary skill in the art.

Non-limiting examples of solid acids can also include both natural and synthetic molecular sieves. Molecular sieves have silicate-based structures ("zeolites") and AlPO-based structures. Some zeolites are silicate-based materials which are comprised of a silica lattice and, optionally, alumina combined with exchangeable cations such as alkali or alkaline earth metal ions. For example, faujasites, mordenites and pentasils are non-limiting illustrative examples of such silicate-based zeolites. Silicate-based zeolites are made of alternating $SiO_2$ and $MO_x$ tetrahedral, where in the formula M is an element selected from Groups 1 through 16 of the Periodic Table (new IUPAC). These types of zeolites have 8-, 10- or 12-membered ring zeolites, such as ZSM-5, ZSM-22, ZSM-48 and ZSM-57.

Other silicate-based materials suitable for use in practicing the present invention include zeolite bound zeolites as described in WO 97/45387, incorporated herein by reference in its entirety. These materials comprise first crystals of an acidic intermediate pore size first zeolite and a binder comprising second crystals of a second zeolite. Unlike zeolites bound with amorphous material such as silica or alumina to enhance the mechanical strength of the zeolite, the zeolite bound zeolite catalyst does not contain significant amounts of non-zeolitic binders.

The first zeolite used in the zeolite bound zeolite catalyst is an intermediate pore size zeolite. Intermediate pore size zeolites have a pore size of from about 5 to about 7 Å and include, for example, AEL, MFI, MEL, MFS, MEI, MTW, EUO, MTT, HEU, FER, and TON structure type zeolites. These zeolites are described in *Atlas of Zeolite Structure Types*, eds. W. H. Meier and D. H. Olson, Butterworth-Heineman, Third Edition, 1992, which is incorporated herein by reference. Non-limiting, illustrative examples of specific intermediate pore size zeolites are ZSM-5, ZSM-11, ZSM-12, ZSM-22, ZSM-23, ZSM-34, ZSM-35, ZSM-38, ZSM-48, ZSM-50 AND ZSM-57. Preferred first zeolites are galliumsilicate zeolites having an MFI structure and alumiminosilicate zeolites having an MFR structure.

The second zeolite used in the zeolite bound zeolite structure will usually have an intermediate pore size (e.g., about 5.0 to about 5.5 Å) and have less activity than the first zeolite. Preferably, the second zeolite will be substantially non-acidic and will have the same structure type as the first zeolite. The preferred second zeolites are aluminosilicate zeolites having a silica to alumina mole ratio greater than 100 such as low acidity ZSM-5. If the second zeolite is an aluminosilicate zeolite, the second zeolite will generally have a silica to alumina mole ratio greater than 100:1, e.g., 500:1; 1,000:1, etc., and in some applications will contain no more than trace amounts of alumina. The second zeolite can also be silicalite, i.e., a MFI type substantially free of alumina, or silicalite 2, a MEL type substantially free of alumina. The second zeolite is usually present in the zeolite bound zeolite catalyst in an amount in the range of from about 10% to 60% by weight based on the weight of the first zeolite and, more preferably, from about 20% to about 50% by weight. The second zeolite crystals, in addition to binding the first zeolite particles and maximizing the performance of the catalyst may, for example, intergrow and form an overgrowth that coats or partially coats the first zeolite crystals. In particular embodiments, the crystals will be resistant to attrition.

The zeolite bound zeolite catalyst may be prepared by a three step procedure. The first step involves the synthesis of the first zeolite crystals prior to converting it to the zeolite bound zeolite catalyst. Next, a silica-bound aluminosilicate zeolite can be prepared, for example, by mixing a mixture comprising the aluminosilicate crystals, a silica gel or sol, water and optionally an extrusion aid and, optionally, a metal component until a homogeneous composition in the form of an extrudable paste develops. The final step is the conversion of the silica present in the silica-bound catalyst to a second zeolite which serves to bind the first zeolite crystals together.

It is to be understood that the above description of zeolite bound zeolites can be equally applied to non-zeolitic molecular sieves (i.e., AlPO's).

Other molecular sieve materials suitable for this invention include aluminophosphate-based materials. Aluminophosphate-based materials are made of alternating AlO4 and PO4 tetrahedra. Members of this family have 8—(e.g., $AlPO_4$-12, -17, -21, -25, -34, -42, etc.) 10—(e.g., $AlPO_4$-11, 41, etc.), or 12—($AlPO_4$-5, -31 etc.) membered oxygen ring channels. Although $AlPO_4$s are neutral, substitution of Al and/or P by cations with lower charge introduces a negative charge in the framework, which is countered by cations imparting acidity.

By turn, substitution of silicon for P and/or a P—Al pair turns the neutral binary composition (i.e., Al, P) into a series of acidic-ternary-composition (Si, Al, P) based SAPO materials, such as SAPO-5, -11, -14, -17, -18, -20, -31, -34, -41, -46, etc. Acidic ternary compositions can also be created by substituting divalent metal ions for aluminum, generating the MeAPO materials. Me is a metal ion which can be selected from the group consisting of, but not limited to Mg, Co, Fe, Zn and the like. Acidic materials such as MgAPO (magnesium substituted), CoAPO (cobalt substituted), FeAPO (iron substituted), MnAPO (manganese substituted) ZnAPO (zinc substituted) etc. belong to this category. Substitution can also create acidic quaternary-composition based materials such as the MeAPSO series, including FeAPSO (Fe, Al, P, and Si), MgAPSO (Mg, Al, P, Si), MnAPSO, CoAPSO, ZnAPSO (Zn, Al, P, Si), etc. Other substituted aluminophosphate-based materials include ElAPO and ElAPSO (where El=B, As, Be, Ga, Ge, Li, Ti, etc.). As mentioned above, these materials have the appropriate acidic strength for reactions such as cracking. The more preferred aluminophosphate-based materials include 10- and 12-membered ring materials (SAPO-11, -31, -41; MeAPO-11, -31, -41; MeAPSO-11, -31, 41; ElAPO-11, -31, -41; ElAPSO-11, -31, -41, etc.) which have significant olefin selectivity due to their channel structure.

Supported acid materials are either crystalline or amorphous materials, which may or may not be themselves acidic, modified to increase the acid sites on the surface. Non-limiting, illustrative examples are $H_2SO_4$, $H_3PO_4$, $H_3BO_3$, $CH_2(COOH)_2$, mounted on silica, quartz, sand, alumina or diatomaceous earth, as well as heteropoly acids mounted on silica, quartz, sand, alumina or diatomaceous earth. Non-limiting, illustrative examples of crystalline supported acid materials are acid-treated molecular sieves, sulfated zirconia, tungstated zirconia, phosphated zirconia and phosphated niobia.

Although the term "zeolites" includes materials containing silica and optionally, alumina, it is recognized that the silica and alumina portions may be replaced in whole or in part with other oxides. For example, germanium oxide, tin oxide, phosphorus oxide, and mixtures thereof can replace the silica portion. Boron, oxide, iron oxide, gallium oxide, indium oxide, and mixtures thereof can replace the alumina portion. Accordingly, "zeolite" as used herein, means not only materials containing silicon and, optionally, aluminum atoms in the crystalline lattice structure thereof, but also materials which contain suitable replacement atoms for such silicon and aluminum, such as gallosilicates, borosilicates, ferrosilicates, and the like.

Besides encompassing the materials discussed above, "zeolites" also encompasses aluminophosphate-based materials.

Mesoporous solid acids can be ordered and/or non-ordered. Non-limiting examples of ordered mesoporous materials include pillared layered clays (PILC's), MCM-41 and MCM-48. Non-limiting examples of non-ordered mesoporous materials include silica and titania-based xerogels and aerogels.

The solid acid can also include ordered mesoporous amorphous materials. Non-limiting examples of ordered mesoporous materials include pillared layered clays (PILC's), MCM-41 and MCM-48.

Figure 2:
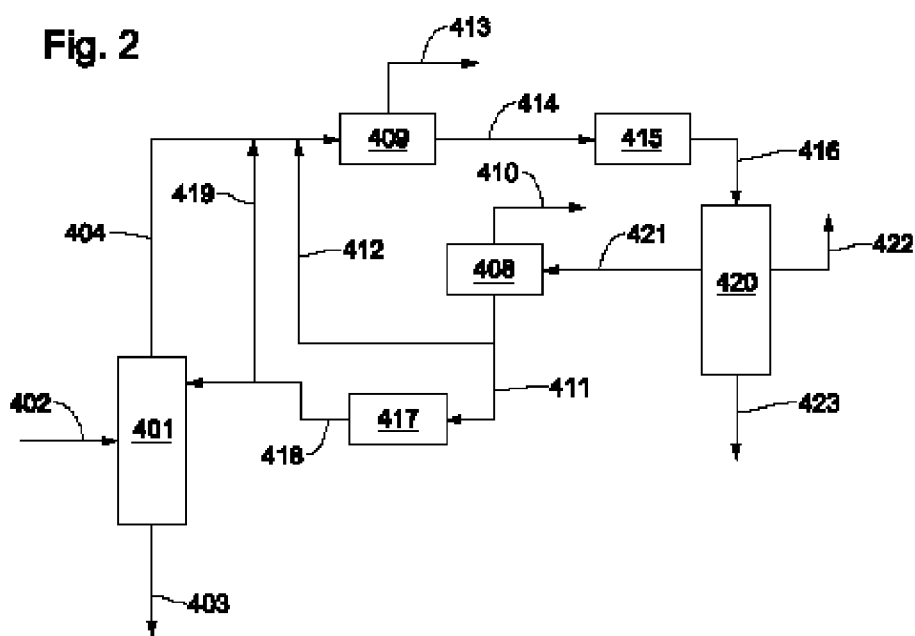
FIG. 2 is a schematic diagram of a producing para-xylene by employing integrated fractional crystallization and selective adsorption according to one or more embodiments of the present invention.

An alternate embodiment is shown in FIG. 2, which process includes a first separating unit 401, which may be one or more distillation columns, that receives a $C_8$+ aromatic hydrocarbon feed stream from line 402 and separates the feed into an overhead vapor stream via line 404 and a bottom liquid stream via 403 in similar fashion to that process described in FIG. 1.

The overhead vapor stream, which is composed mainly of $C_8$ aromatic hydrocarbons, is fed via line 404 to the selective adsorption unit 409, where a PX-rich product stream is recovered through line 413 and a PX-depleted stream is withdrawn via line 414. The PX-depleted stream is fed by line 414 to a xylene isomerization unit 415 where the stream is converted into an isomerized stream having higher PX concentration than that of the stream fed to isomerization unit 415.

The isomerized stream is removed from xylene isomerization unit 415 by line 416 and is fed to a separating unit 420, which may be one or more distillation columns. Separation unit 420 separates and transfers $C_7$− hydrocarbons via line 422, $C_9$+ hydrocarbons via line 423, and $C_8$ hydrocarbons via line 421. The $C_8$ hydrocarbon rich stream is fed by line 421 to a fractional crystallization unit 408, where a PX-rich product stream is recovered through line 410 and a PX-depleted raffinate stream is withdrawn via line 411.

A second xylene isomerization unit 417 treats all or part of the PX-depleted raffinate stream withdrawn from the fractional crystallization unit 408 via line 411. When unit 417 treats part of the PX-depleted raffinate stream, the remaining portion of the raffinate stream could be sent to the selective adsorption unit 409 via 412 and optionally 404.

In one or more embodiments, second xylene isomerization unit 417 is a liquid-phase isomerization unit. The effluent stream from second xylene isomerization unit 417, which has a higher PX concentration than the PX-depleted raffinate stream, is withdrawn through line 418 and ultimately fed to selective adsorption unit 409. In this way, the overall PX content of the feed recycled back to selective adsorption unit 409 can be increased. In one or more embodiments, the liquid-phase isomerization product contains mostly equilibrium or near equilibrium xylenes.

In one or more embodiments, all or part of the effluent stream from second xylene isomerization unit 417 is sent directly to first separating unit 401 via 418. In one or more embodiments, line 418 may direct the effluent to a proper tray position to affect the separation of $C_8$ and $C_9$+ hydrocarbons.

In other embodiments, all or part of the effluent stream from second xylene isomerization unit 417 is sent directly to selective adsorption unit 409 via 419 and optionally line 404. In one or more embodiments, the effluent stream from second xylene isomerization unit 417 (i.e., the isomerized stream) is sent directly to selective adsorption unit 409 without further processing (particularly processing to remove or reduce $C_7$− or $C_9$+ hydrocarbons). In other embodiments, the isomerized stream from isomerization unit 417 is further treated, such as by fractionation, to remove at least a part of the $C_7$− and $C_9$+ hydrocarbons formed in isomerization unit 417 and then sent directly to selective adsorption unit 409.

Thus, the process depicted in FIG. 2 likewise includes an integrated fractional crystallization unit and selective adsorption unit with a liquid-phase isomerization process increasing the PX concentration of the feed effluent stream from the factional crystallization that is directed toward the selective adsorption unit.

As with the previous embodiments, the isomerization process within xylene isomerization unit 417 is manipulated to produce a PX-rich stream having less than 1,000 ppm, in other embodiments less than 500 ppm, and in other embodiments less than 300 ppm, and in other embodiments less than 250 ppm benzene.

In one or more embodiments, the operation of liquid-phase isomerization unit 417 is manipulated to produce a PX-rich stream having less than 5,000 ppm, in other embodiments less than 4,000 ppm, in other embodiments less than 3,000 ppm, in other embodiments less than 2,000 ppm, in other embodiments less than 1,000 ppm, and in other embodiments less than 500 ppm $C_9+$ hydrocarbons (e.g., aromatics).

In one or more embodiments, liquid-phase isomerization unit 417 is operated at or below 300° C., in other embodiments below 280° C., and in other embodiments below 260° C. In these or other embodiments, liquid-phase isomerization unit 417 is operated at or above 150° C., in other embodiments above 175° C., and in other embodiments above 200° C.

In one or more embodiments, liquid-phase isomerization unit 417 is operated at a pressure below 350 psi, in other embodiments below 300 psi, and in other embodiments below 270 psi. In these or other embodiments, liquid-phase isomerization unit 417 is operated at a pressure above 30 psi, in other embodiments above 75 psi, and in other embodiments above 125 psi.

In one or more embodiments, the flow rate of the PX-depleted raffinate stream through isomerization unit 417 is at least 0.1 weight hourly space velocity (WHSV), in other embodiments at least 1.0 WHSV, in other embodiments at least 2.0 WHSV, and in other embodiments at least 5.0 WHSV. In these or other embodiments, the flow rate of the PX-depleted raffinate stream through isomerization unit 417 is less than 100 WHSV, and in other embodiments less than 50 WHSV, in other embodiments less than 10 WHSV.

In one or more embodiments, liquid-phase isomerization unit 417 includes a solid acid catalyst as described above with respect to the previous embodiments.

Specific Embodiments

Paragraph A: A process for producing a PX-rich product, the process comprising: (a) separating a feedstock containing $C_8$ hydrocarbons to produce a $C_8$ hydrocarbons rich stream; (b) separating a first portion of the $C_8$ hydrocarbons rich stream to produce a first PX-rich stream and a first raffinate stream; (c) isomerizing at least a portion of the first raffinate stream to produce a first isomerized stream having a higher PX concentration than the first raffinate stream; (d) separating a second portion of the $C_8$ hydrocarbons rich stream to produce a second PX-rich stream and a second raffinate stream; (e) isomerizing, at least partially in the liquid phase, at least a portion of the second raffinate stream to produce a second isomerized stream having a higher PX concentration than the second raffinate stream, where the second isomerized stream has a benzene concentration of less than 1,000 ppm and a $C_9+$ hydrocarbons concentration of less than 5,000 ppm; (f) recovering at least a portion of at least one of the first and second PX-rich streams as PX-rich product; and (g) providing at least a portion of the first isomerized stream and at least a portion of the second isomerized stream to the separating (a).

Paragraph B: The process of paragraph A, where the second isomerized stream has a higher PX concentration than the second raffinate stream and a benzene concentration of less than 500 ppm and a $C_9+$ hydrocarbons concentration of less than 3,000 ppm.

Paragraph C: The process of paragraphs A-B, where the second isomerized stream has a higher PX concentration than the second raffinate stream and a benzene concentration of less than 300 ppm and a $C_9+$ hydrocarbons concentration of less than 2,000 ppm.

Paragraph D: The process of paragraphs A-C, where said step of isomerizing (e) takes place at a temperature at or below 300° C.

Paragraph E: The process of paragraphs A-D, where said step of isomerizing (e) takes place at a temperature at or below 280° C.

Paragraph F: The process of paragraphs A-E, where the flow rate of the second raffinate stream during said step of isomerizing (e) is at least 0.1 WHSV.

Paragraph G: The process of paragraphs A-F, where the flow rate of the second raffinate stream during said step of isomerizing (e) is at least 2.0 WHSV.

Paragraph H: The method of paragraphs A-G, where said step of isomerizing (e) employs a molecular sieve catalyst.

Paragraph I: The method of paragraphs A-H, where said step of isomerizing (e) employs a zeolite catalyst of MFI structure.

Paragraph J: The method of paragraphs A-I, where said step of isomerizing (e) employs a ZSM-5 catalyst.

Paragraph K: The method of paragraphs A-J, where said step of isomerizing (c) takes place at least partially in the vapor phase.

Paragraph L: The method of paragraphs A-K, where said step of recovering (f) includes selective adsorption.

Paragraph M: The method of paragraphs A-L, where said separating (d) includes fractional crystallization.

Paragraph N: The method of paragraphs A-M, providing at least a portion of the second raffinate stream to said separating (b).

Paragraph O: The method of paragraphs A-N, providing at least a portion of the second isomerized stream to said separating (b).

Paragraph P: A process for producing a PX-rich product, the process comprising: (a) separating a feedstock containing $C_8$ hydrocarbons to produce a $C_8$ hydrocarbons rich stream; (b) separating a first portion of the $C_8$ hydrocarbons rich stream to produce a first PX-rich stream and a first raffinate stream; (c) isomerizing at least a portion of the first raffinate stream to produce a first isomerized stream having a higher PX concentration than the first raffinate stream; (d) separating the first isomerized stream to produce a second $C_8$ hydrocarbons rich stream; (e) separating the second $C_8$ hydrocarbons rich stream to produce a second PX-rich stream and a second raffinate stream; (f) isomerizing, at least partially in the liquid phase, at least a portion of the second raffinate stream to produce a second isomerized stream having a higher PX concentration than the second raffinate stream; and (g) providing at least a portion of the second isomerized stream to the separating (a).

Paragraph Q: The method of paragraph P, where said separating (b) includes selective adsorption.

Paragraph R: The method of paragraphs P-Q, where said step of isomerizing (c) takes place at least partially in the vapor phase.

Paragraph S: The method of paragraphs P-R where said separating (e) includes fractional crystallization. Paragraph T: The process of paragraphs Paragraph T: The method of paragraphs P-S, where the second isomerized stream has a benzene concentration of less than 1,000 ppm and a $C_9+$ hydrocarbons concentration of less than 5,000 ppm.

Paragraph U: The method of paragraphs P-T, where said step of isomerizing (f) takes place at a temperature at or below 300° C.

Paragraph V: The method of paragraphs P-U, providing at least a portion of the second raffinate stream to said separating (b).

Paragraph W: The method of paragraphs P-V providing at least a portion of the second isomerized stream to said separating (b).

Paragraph X: The method of paragraphs P-W, further comprising the step of separating at least a portion of the second isomerized stream to remove at least a portion of $C_7$– and $C_9+$ hydrocarbons generated in said isomerizing (f) and subsequently providing the second isomerized stream to said separating (b).

Paragraph Y: A process for producing a PX-rich product, the process comprising: (a) separating a feedstock containing $C_8$ hydrocarbons to produce a $C_8$ hydrocarbons rich stream; (b) separating a first portion of the $C_8$ hydrocarbons rich stream to produce a first PX-rich stream and a first raffinate stream; (c) isomerizing at least a portion of the first raffinate stream to produce a first isomerized stream having a higher PX concentration than the first raffinate stream; (d) separating the first raffinate stream to produce a second $C_8$ hydrocarbons rich stream; (e) separating the second $C_8$ hydrocarbons rich stream to produce a second PX-rich stream and a third stream; (f) isomerizing, at least partially in the liquid phase, at least a portion of the second raffinate stream to produce a second isomerized stream having a higher PX concentration than the second raffinate stream, where the second isomerized stream has a benzene concentration of less than 1,000 ppm and a $C_9+$ hydrocarbons concentration of less than 5,000 ppm; and (g) providing at least a portion of the second isomerized stream to the separating (a).

Paragraph Z: The process of paragraph Y, where the second isomerized stream has a higher PX concentration than the second raffinate stream and a benzene concentration of less than 500 ppm, and a $C_9+$ hydrocarbons concentration of less than 3,000 ppm.

Paragraph AA: The process of paragraphs Y-Z, where the second isomerized stream has a higher PX concentration than the second raffinate stream and a benzene concentration of less than 300 ppm, and a $C_9+$ hydrocarbons concentration of less than 2,000 ppm.

Paragraph BB: The process of paragraphs Y-AA, where said step of isomerizing (f) takes place at a temperature at or below 300° C.

Paragraph CC: The process of paragraphs Y-BB, where said step of isomerizing (f) takes place at a temperature at or below 280° C.

Paragraph DD: The process of paragraphs Y-CC, where the flow rate of the second raffinate stream during said step of isomerizing (f) is at least 0.1 WHSV.

Paragraph EE: The process of paragraphs Y-DD, where the flow rate of the second raffinate stream during said step of isomerizing (f) is at least 2.0 WHSV.

Paragraph FF: The method of paragraphs Y-EE, where said step of isomerizing (f) employs a molecular sieve catalyst.

Paragraph GG: The method of paragraphs Y-FF, where said step of isomerizing (f) employs a zeolite catalyst of MFI structure.

Paragraph HH: The method of paragraphs Y-GG, where said step of isomerizing (f) employs a ZSM-5 catalyst.

Paragraph II: The method of paragraphs Y-HH, providing at least a portion of the second raffinate stream to said separating (b).

Paragraph JJ: The method of paragraphs Y-II, providing at least a portion of the second isomerized stream to said separating (b).

Paragraph KK: In a PX-production process where a $C_8$ hydrocarbon rich stream is separated into a PX-rich stream and a PX-depleted stream by fractional crystallization, and where the PX-depleted stream is subsequently isomerized to increase the concentration of PX in the PX-depleted stream for subsequent separation by selective adsorption, the improvement comprising isomerizing said PX-depleted stream in the liquid phase to produce a stream having a higher PX concentration than the PX-depleted stream, a benzene concentration of less than 500 ppm, and a $C_9+$ concentration of less than 5,000 ppm.

Paragraph LL: The process of paragraph KK, where said stream having a higher PX concentration than the PX-depleted stream has a benzene concentration of less than 500 ppm and a $C_9+$ hydrocarbons concentration of less than 3,000 ppm.

Paragraph MM: The process of paragraphs KK-LL, where said stream having a higher PX concentration than the PX-depleted stream has a benzene concentration of less than 300 ppm and a $C_9+$ hydrocarbons concentration of less than 2,000 ppm.

Paragraph NN: The process of paragraphs KK-MM, where said step of isomerizing the PX-depleted stream in the liquid phase takes place at a temperature at or below 300° C.

Paragraph OO: The process of paragraphs KK-NN, where said step of isomerizing the PX-depleted stream in the liquid phase takes place at a temperature at or below 280° C.

Paragraph PP: The process of paragraphs KK-OO, where said step of isomerizing the PX-depleted stream in the liquid phase takes place at a flow rate of at least 0.1 WHSV.

Paragraph QQ: The process of paragraphs KK-PP, where said step of isomerizing the PX-depleted stream in the liquid phase takes place at a flow rate of at least 2.0 WHSV.

Paragraph RR: The method of paragraphs KK-QQ, where said step of isomerizing the PX-depleted stream in the liquid phase employs a molecular sieve catalyst.

Paragraph SS: The method of paragraphs KK-RR, where said step of isomerizing the PX-depleted stream in the liquid phase employs a zeolite catalyst of MFI structure.

Paragraph TT: The method of paragraphs KK-SS, where said step of isomerizing the PX-depleted stream in the liquid phase employs a ZSM-5 catalyst.

Paragraph UU: A process for producing a PX-rich product, the process comprising: (a) providing a PX-depleted stream; (b) isomerizing at least a portion of the PX-depleted stream to produce an isomerized stream having a PX concentration greater than the PX-depleted stream and a benzene concentration of less than 1,000 ppm and a $C_9+$ hydrocarbons concentration of less than 5,000 ppm; and (c) separating the isomerized stream by selective adsorption.

EXAMPLES

A $C_8+$ hydrocarbon stream was treated in accordance with the process depicted in FIG. 2. Liquid-phase isomerization was conducted at 417 using a ZSM-5 zeolite catalyst at 265 psig and 3 WHSV. The temperature of isomerization was varied as set forth in Table II. The concentration of various hydrocarbon constituents within the stream was measured before and after the liquid-phase isomerization unit. Also, consistent with FIG. 2, the stream was subsequently treated by vapor-phase isomerization. The concentration of various constituents within the stream was measured before and after the vapor-phase isomerization.

TABLE II

| Examples | — | 1 | Δ1 | 2 | Δ2 | 3 | Δ3 | — | 4 | Δ4 |
|---|---|---|---|---|---|---|---|---|---|---|
| Stream | Feed to Liquid Phase | Liquid Phase effluent | Liquid Phase Effluent | Liquid Phase Effluent | Liquid Phase Effluent | Liquid Phase Effluent | Liquid Phase Effluent | Feed to Vapor Phase | Vapor Phase effluent | Vapor Phase effluent |
| Temp. | — | 246° C. | 246° C. | 241° C. | 241° C. | 236° C. | 236° C. | — | — | — |
| Benzene | 0.008 | 0.022 | 0.014 | 0.019 | 0.011 | 0.015 | 0.007 | 0.001 | 4.95 | 4.949 |
| Toluene | 0.963 | 1.077 | 0.114 | 1.035 | 0.072 | 1.006 | 0.043 | 0.485 | 1.595 | 1.11 |
| Ethyl Benzene | 2.956 | 2.881 | −0.075 | 2.901 | −0.055 | 2.93 | −0.026 | 9.281 | 1.856 | −7.425 |
| Para-Xylene | 12.514 | 21.168 | 8.654 | 20.184 | 7.67 | 19.035 | 6.521 | 0.971 | 20.345 | 19.374 |
| Meta-Xylene | 62.621 | 51.572 | −11.049 | 53.27 | −9.351 | 54.907 | −7.714 | 63.021 | 45.932 | −17.089 |
| Ortho-Xylene | 16.625 | 18.849 | 2.224 | 18.19 | 1.565 | 17.731 | 1.106 | 23.258 | 19.956 | −3.302 |
| $C_9$ Aromatics | 0 | 0.115 | 0.115 | 0.057 | 0.057 | 0.045 | 0.045 | 0.103 | 0.667 (as $C_9$ and $C_{10}+$) | 0.564 |
| $C_{10}+$ Aromatics | 0 | 0.082 | 0.082 | 0.041 | 0.041 | 0.033 | 0.033 | — | — | — |
| Non-Aromatics | 4.31 | 4.231 | −0.079 | 4.3 | −0.01 | 4.295 | −0.015 | 2.88 | 4.683 | 1.803 |
| Hydrogen | — | 0 | 0 | 0 | 0 | 0 | 0 | 0 | 0.016 | 0.016 |
| Totals | 99.997 | 99.997 | 0 | 99.997 | 0 | 99.997 | 0 | 100 | 99.333 | — |

The data in Table II shows that the production of benzene and toluene is markedly lower when liquid-phase isomerization is compared to vapor-phase isomerization. Also, the data shows the significant temperature dependence of benzene production even in the liquid phase. Notably, at 246° C., the benzene concentration was at 220 ppm, which is below the 300 ppm threshold. While within critical thresholds, it is noted that this amount represents nearly a two-fold increase in the amount of benzene present after liquid-phase isomerization at 236° C.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. In a PX-production process where a $C_8$ hydrocarbon rich stream is separated into a PX-rich stream and a PX-depleted stream by fractional crystallization, and where the PX-depleted stream is subsequently isomerized to increase the concentration of PX in the PX-depleted stream for subsequent separation by selective adsorption, the improvement comprising isomerizing said PX-depleted stream in the liquid phase to produce a stream having a higher PX concentration than the PX-depleted stream, a benzene concentration of less than 300 ppm, and a $C_9+$ hydrocarbon concentration of less than 3,000 ppm.

2. The process of claim 1, wherein said selective adsorption produces a PX-rich stream and a PX-depleted stream.

3. The process of claim 1, wherein at least a portion of said isomerized stream is treated to remove said C9+ hydrocarbon prior to said selective adsorption.

4. The process of claim 1, wherein at least a portion of said isomerized stream is treated to remove said benzene prior to said selective adsorption.

* * * * *